US011160879B2

(12) United States Patent
Yamamoto

(10) Patent No.: US 11,160,879 B2
(45) Date of Patent: Nov. 2, 2021

(54) TRANSGENIC ANIMAL FOR VISUALIZATION OF ATP AND USE THEREOF

(71) Applicant: Masamichi Yamamoto, Kyoto (JP)

(72) Inventor: Masamichi Yamamoto, Kyoto (JP)

(73) Assignee: Masamichi Yamamoto, Kyoto (JP)

( * ) Notice: Subject to any disclaimer, the term of this patent is extended or adjusted under 35 U.S.C. 154(b) by 612 days.

(21) Appl. No.: 15/111,730

(22) PCT Filed: Jan. 15, 2015

(86) PCT No.: PCT/JP2015/050932
§ 371 (c)(1),
(2) Date: Dec. 29, 2017

(87) PCT Pub. No.: WO2015/108102
PCT Pub. Date: Jul. 23, 2015

(65) Prior Publication Data

US 2018/0110880 A1 Apr. 26, 2018

(30) Foreign Application Priority Data

Jan. 15, 2014 (JP) ............................ JP2014-005429

(51) Int. Cl.
*A61K 49/00* (2006.01)
*A01K 67/027* (2006.01)
*C12N 15/85* (2006.01)
*C12N 9/14* (2006.01)
*C12N 15/90* (2006.01)

(52) U.S. Cl.
CPC ...... *A61K 49/0008* (2013.01); *A01K 67/0275* (2013.01); *C12N 9/14* (2013.01); *C12N 15/8509* (2013.01); *C12Y 306/03* (2013.01); *A01K 2217/07* (2013.01); *A01K 2217/072* (2013.01); *A01K 2217/15* (2013.01); *A01K 2217/20* (2013.01); *A01K 2227/105* (2013.01); *A01K 2267/0356* (2013.01); *A01K 2267/0375* (2013.01); *A01K 2267/0393* (2013.01); *C07K 2319/60* (2013.01); *C12N 15/907* (2013.01); *C12N 2015/8527* (2013.01); *C12N 2830/00* (2013.01); *C12N 2830/15* (2013.01)

(58) Field of Classification Search
CPC ............ A01K 67/0275; A01K 67/0276; A01K 67/0278; C12N 15/8509
See application file for complete search history.

(56) References Cited

U.S. PATENT DOCUMENTS 6,461,864 B1 * 10/2002 Soriano .............. A01K 67/0275 435/325
6,586,251 B2 7/2003 Economides et al.
2006/0293273 A1 12/2006 Mangano
2010/0233692 A1 * 9/2010 Noji ...................... C07K 14/00 435/6.13
2013/0243759 A1 9/2013 Friedrich et al.

FOREIGN PATENT DOCUMENTS

EP 1 226 752 A1 7/2002
JP 2002-000121 A 1/2002
JP 2007-252370 A 10/2007
WO 2001/033957 A1 5/2001
WO 2006/105167 A2 10/2006
WO 2008/117792 A1 10/2008
WO WO-2008117792 A1 * 10/2008 ............ C07K 14/00

OTHER PUBLICATIONS

Thunemann et al Cir. Res, 113, 4, 365-371 (Year: 2013).*
Thunemann et al Circ Res. 113:365-371 (Year: 2013).*
Zhang et al American J Physiol, 299, 3, H946-H956 (Year: 2010).*
Bronson et al Proc Natl Acad Sci USA 93, 9067-9072 (Year: 1996).*
Skolnick et al Trends in Biotech, 18, 34-39 (Year: 2000).*
Davis, New Biologist, 2(5), 410-419 (Year: 1990).*
Ngo et al., The protein Folding Problem and Tertiary Structure Prediction, pp. 492-495 (Year: 1994).*
Rudingerin Peptide Hormones, Parsons (ed.), University Park Press: Baltimore, MD, pp. 1-7 (Year: 1976).*
Kato-Yamada et al J Biol. Chemistry ;278(38):36013-6 (Year: 2003).*
Barthold S., Genetica, vol. 122, pp. 75-88 (Year: 2004).*
Heimain-Patterson Amyotrophic Lateral Schlerosis, vol. 00, pp. 1-8 (Year: 2011).*
Tong et al. Nature, vol. 467(7312), 211-213 (Year: 2010).*
Hong et al. Stem Cells and Development, vol. 21(9), . 1571-1586 (Year: 2012).*
Munoz et al. Stem Cell Rev. and Rep., vol. 5, 6-9 (Year: 2009).*
Dow et al (Trends in Molecular Medicine, 21, 609-621 (Year: 2015).*
Kosicki et al Nature Biotechnology, 1-8 (Year: 2018).*
Tong et al Nature Protocol, 827-844 (Year: 2011).*
Chen et al PLoS One, 6, 8, e23376, 1-8 (Year: 2011).*
Tchorz et al PLoS One, 7(1), e30011, 1-(Year: 2012).*

(Continued)

*Primary Examiner* — Anoop K Singh
(74) *Attorney, Agent, or Firm* — Lathrop GPM LLP; James H. Velema; Judith L. Stone-Hulslander

(57) ABSTRACT

Provided are a transgenic non-human mammal expressing a fusion protein, wherein the fusion protein comprises an ε subunit of an ATP synthase and two distinct fluorescent proteins as a donor and an acceptor for FRET, one of the fluorescent proteins being placed at an amino terminal moiety of the ε subunit and the other being placed at a carboxyl terminal moiety of the ε subunit, and a method of screening for an agent for preventing or treating diseases in a mammal in need thereof, comprising using an above transgenic non-human mammal.

6 Claims, 11 Drawing Sheets
(4 of 11 Drawing Sheet(s) Filed in Color)
Specification includes a Sequence Listing.

(56) References Cited

OTHER PUBLICATIONS

Aoki et al. (Feb. 7, 2013) "Fluorescence resonance energy transfer imaging of cell signaling from in vitro to in vivo: Basis of biosensor construction, live imaging, and image processing," Devlop. Growth Differ. 55:515-522.

Thunemann et al. (Aug. 2, 2013) "Transgenic Mice for cGMP Imaging," Circ. Res. 113(4):365-371.

Utena et al. (1966) "Behavioral Aberrations in Methamphetamine-intoxicated Animals and Chemical Correlates in the Brain," Progress in Brain Research. 21(Part B):192-207.

Willemse et al. (2007) "ATP and FRET—a cautionary note," Nat. Biotechnol. 25(2):170-172.

Zang et al. (2010) "In vivo assessment of artery smooth muscle [Ca2+]i and MLCK activation in FRET-based biosensor mice," Am. J. Physiol. Heart Circ. Physiol. 299:H946-H956.

International Preliminary Report on Patentability corresponding to International Patent Application No. PCT/JP2015/050932, dated Jul. 21, 2016.

International Search Report corresponding to International Patent Application No. PCT/JP2015/050932, dated Apr. 7, 2015.

Gucy1b1 <tm1.1Frb> Targeted Allele Detail MGI Mouse (MGI_3710142), 1 page.

Hara et al. (2004) "Imaging endoplasmic reticulum calcium with a fluorescent biosensor in transgenic mice," Am J Physiol Cell Physiol, 287, pp. C932-C938.

Li et al. (2008) "Germline Competent Embryonic Stem Cells Derived from Rat Blastocysts," Cell, 135, pp. 1299-1310.

* cited by examiner

TRANSGENIC ANIMAL FOR VISUALIZATION OF ATP AND USE THEREOF

RELATED APPLICATIONS

This application is a 35 U.S.C. § 371 filing of International Application No. PCT/JP2015/050932, filed Jan. 15, 2015, which claims priority to Japanese Patent Application No. 2014-005429, filed Jan. 15, 2014. The content of each of these applications is incorporated herein by reference in their entirety.

Color Drawings

The patent or application file contains at least one drawing executed in color. Copies of this patent or patent application publication with color drawing(s) will be provided by the Office upon request and payment of the necessary fee.

TECHNICAL FIELD

The present invention relates to a transgenic mammal for visualization of ATP and a use thereof. According to the present invention, changes in the level and the distribution of ATP can be monitored in vivo.

BACKGROUND ART

Adenosine triphosphate (ATP) is used in many biological reactions and called "cellular energy currency". Monitoring ATP levels is accordingly important to assess the energy status in a living body. Methods conventionally and widely used to measure cellular ATP levels include a luciferase assay that includes the steps of: obtaining cells from an animal; measuring the weight of the cells or counting the number of the cells; homogenizing the cells; adding to the cell homogenate a composition containing luciferase as a main component; measuring the luminescence intensity; and estimating the ATP level. Luciferase assays are unsuitable for measuring cellular ATP levels precisely for the following reasons: the assays are highly sensitive while cause large measurement errors; the luminescence intensity varies depending on time after the addition of the composition comprising luciferase, the oxygen concentration and the pH of the solution to be measured; the precise number of the cells can hardly be estimated; and the assay result varies depending on procedures for homogenizing the cells. In addition, homogenization of a cell destroys its subcellular compartments including cytoplasm and cell organelles such as mitochondria, thereby being unable to measure the ATP level at each of the cellular compartments or the time-dependent ATP levels.

Other methods for measuring ATP levels in cells or organs include a mass spectroscopy assay, which comprises the steps of: pre-treating the cells or organs; and measuring the ATP level with a mass spectroscopy detector. Mass spectroscopy also have some problems: the assay requires a large number of cells and can hardly be performed with a single cell; the pre-treatment such as homogenization of the cells leads large measurement errors and destroys the subcellular compartments including cytoplasm and cell organelles such as mitochondria, thereby being unable to measure the ATP level at each of subcellular compartments or the time-dependent ATP levels.

Methods using fluorescence resonance energy transfer (FRET) have been recently reported (non-patent literature 1). The method utilizes a fusion protein that includes a cyan fluorescent protein (CFP) and a yellow fluorescent protein (YFP) which are fused to the CBS domain of inosine monophosphate dehydrogenase 2 (IMPDH2). IMPDH2 can react with adenosine nucleic acids such as ATP, adenosine diphosphate (ADP) and adenosine monophosphate (AMP). Patent literature 1 discloses a method for measuring the ATP level using FRET which utilizes a fluorescence-labeled fusion protein including an ε protein derived from an ATP synthase F0F1 ATP-sensitive peptide of Bacillus subtilis and two distinct fluorescent proteins, which are connected to the εprotein. The two fluorescent proteins act as a donor and an acceptor for FRET. However, it still remains difficult to quantitatively measure the time-dependent level or distribution of ATP in a single living cell.

CITATION LIST

Patent Literature

Patent Literature 1. WO2008/117792

Non-Patent Literature

Non-Patent Literature 1. Nat Biotechnol 2007; 25 (2): 170-172.

SUMMARY OF INVENTION

An object of the present invention is to provide a method for quantitatively measuring the cellular ATP level, the subcellular distribution of ATP and time-dependent changes in ATP levels in a single cell of a non-human mammal. Another object is to provide a transgenic animal that is useful for evaluating various disease conditions by quantitatively evaluating the bodily conditions with the ATP levels determined by the above method and also for screening candidate materials for preventing or treating various diseases.

Solution to Problem

The present inventor has intensively studied and successfully generated a mouse expressing a fusion protein which includes the ε subunit of an ATP synthase and two distinct fluorescent proteins bound to the amino terminal moiety and the carboxyl terminal moiety of the ε subunit, respectively. The fluorescent proteins function as a donor and an acceptor in the fluorescence resonance energy transfer (FRET). The present inventor has found that the mouse enables to quantify time-dependent changes in the level or distribution of ATP in a cell or an organ. In addition, the present inventor has found that the mouse is useful for screening substances for preventing or treating several diseases. The present invention has accordingly been made.

Embodiments of the present invention are as follows:

1) A transgenic non-human mammal expressing a fusion protein, wherein the fusion protein comprises the ε subunit of an ATP synthase and two distinct fluorescent proteins that function as a donor and acceptor in FRET and are bound to the amino and carboxyl terminal moieties of the ε subunit, respectively.
2) The transgenic non-human mammal according to (1), wherein the ε subunit comprises an amino acid sequence of SEQ ID NO: 1 or 2.
3) The transgenic non-human mammal according to (1 or 2), wherein the two distinct fluorescent proteins are a combination of two proteins that can cause FRET and each of the two proteins is selected from the group consisting of a cyan fluorescent protein (CFP), a yellow fluorescent protein (YFP), a blue fluorescent protein (BFP), a green fluorescent protein (GFP), a red fluorescent protein (RFP) and an kusabira-orange protein (KO).

4) The transgenic non-human mammal according to any one of (1 to 3), comprising a DNA encoding the fusion protein, wherein the DNA is inserted into the ROSA26 locus on the chromosome of the transgenic mammal.

5) The transgenic non-human mammal according to any one of (1 to 4), wherein the DNA encoding the fusion protein comprises the lox sequences and the fusion protein is expressed when the region sandwiched between the lox sequences is removed with Cre recombinase.

6) The transgenic non-human mammal according to any one of (1 to 5), wherein the DNA encoding the fusion protein is operably linked to a CAG promoter sequence.

7) A transgenic non-human mammal, which is produced by mating the transgenic non-human mammal according to any one of (1 to 6) with a disease model animal.

8) The transgenic non-human mammal according to (7), wherein the disease model animal is an autism model animal or a heart disease model animal.

9) The transgenic non-human mammal according to any one of (1 to 8), being a mouse.

10) A method of measuring an ATP level in the transgenic non-human animal expressing the fusion protein according to any one of (1 to 9), or in a cell, an organ or tissue obtained therefrom, comprising the steps of: contacting the transgenic non-human animal, the cell, the organ or the tissue with a test substance; and estimating the ATP level from the measured fluorescence intensities emitted from the fusion protein.

11) A method of screening for a drug or evaluating the efficacy of a test substance, comprising the steps of: measuring the ATP level according to the method of claim 10, and evaluating the efficacy of the substance from the measured ATP level.

Advantageous Effects of Invention

The present invention enables to measure quantitatively a time-dependent level or distribution of ATP in a single cell as well as in a non-human mammal. The present invention enables to measure precisely the ATP level in a living cell within a measurement error of 4%, without destroying the subcellular compartments. In addition, the measurement according to the present invention is not affected from changes of oxygen concentration. The measurement enables to measure quantitatively the ATP level in a subcellular compartment. The measurement enables to investigate the distribution of ATP in detail in a non-human mammal embryo during the developmental period.

DESCRIPTION OF EMBODIMENTS

Figure 1:
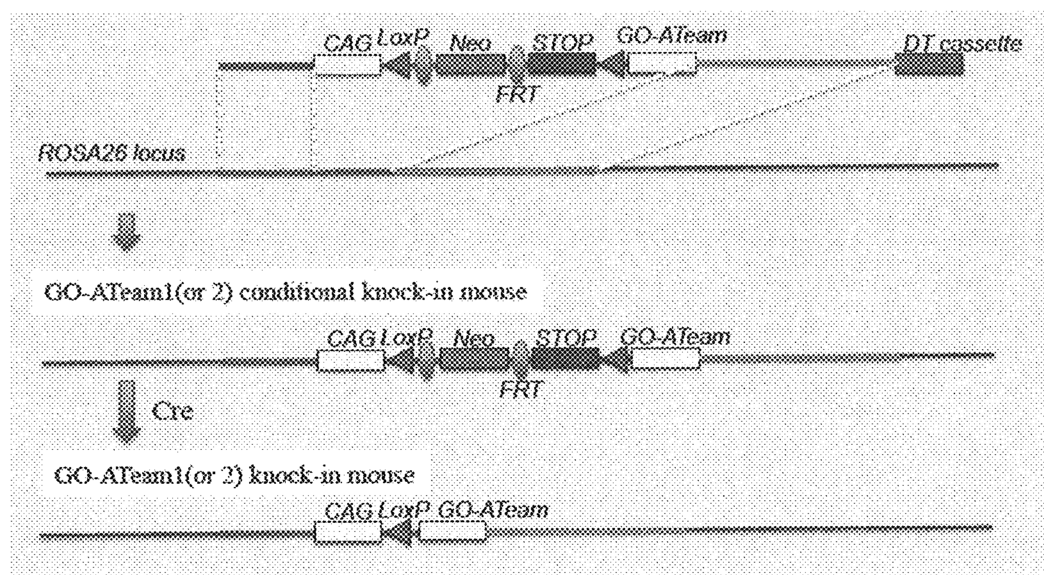
FIG. 1 is a schematic diagram of a construct for expression of GO-ATeam.

The present invention is described in detail below.

The present invention provides a transgenic non-human mammal, which is expressing a fusion protein comprising the ε subunit of F0F1 ATPase and two distinct fluorescent proteins that function as a donor and acceptor for FRET and are bound to the amino and carboxyl terminal moieties of the ε subunit, respectively. The F0F1 ATPase is an ATP synthase derived from Bacillus subtilis and its ε subunit is an ATP sensitive peptide. The fusion protein is also hereinafter referred to "fluorescence-labeled fusion protein". The transgenic non-human mammal according to the present invention may be any non-human mammal species such as mouse, rat, rabbit, goat, pig, dog, cat, guinea pig, hamster, sheep, cow, and marmoset.

ATP synthases are classified into F- and V-ATPases. The F-ATPase consists of two domains: $F_0$ domain and $F_1$ domain. The $F_1$ domain comprises alpha (α), beta (β), gamma (γ), delta (δ) and epsilon (ε) subunits. The ε subunit has a high binding affinity to ATP while it has no or little binding affinity to the other nucleotides such as ADP, dATP and GTP. The structure of the ε subunit changes upon binding to ATP, and is therefore, available for detecting ATP.

The ε subunit of F1-ATPase used in the present invention may be those originated from any biological species. Epsilon subunits obtained from bacterial strains such as *Bacillus* sp, PS3 (GenBank accession No. AB044942; SEQ. ID, NO. 1) and Bacillus subtilis (GenBank accession No, Z28592; SEQ. ID. NO. 2) may be preferable for convenient operability. Epsilon subunits obtained from bacterial strains other than the above may also be used. Epsilon subunits have different binding affinities to ATP depending on their origins (J. Biological Chemistry 2003; 278, 36013-36016 and FEBS Letters 2005; 579, 6875-6878). For example, an ε subunit that can bind to ATP at relatively low concentrations and another ε subunit that can bind to ATP at relatively high concentrations, such as those in a cell. By selecting epsilon subunits with proper affinities, an agent that can bind to various concentration of ATP can be provided.

The ε subunit includes two domains, N- and C-terminal domains. The N-terminal domain includes an amino acid sequence from the N-terminal to around $85^{th}$ amino acid of the ε subunit and forms ten beta strands. The C-terminal domain includes an amino acid sequence from the C-terminal to around $45^{th}$ amino acid of the ε subunit and forms two alpha helices. The C-terminal domain forms a crystal structure in the absence of other subunits of the ATP synthase, while it forms a stretched structure in the presence of the γ subunit of the ATP synthase. Biological experimental data indicate that the structure of the C-terminal domain of the ε subunit changes depending on the presence or absence of ATP, when the ε subunit is contained in a complex comprising the γ subunit and other subunits of the ATP synthase. The C-terminal domain of the ε subunit in the complex forms a stretched structure in the absence of ATP while it forms a compact fold in the presence of ATP. Taking these into consideration, the C-terminal domain of the ε subunit forms a stretched structure or a random structure in the absence of ATP, while it forms a folded compact structure when ATP binds to it.

The ε subunit according to the present invention may include the whole amino acid sequence of the subunit or a fragment thereof. The fragments may be any fragment whose structure changes upon binding to ATP. For example, the ε subunit according to the present invention may include the above N- and C-terminal domains whose structures change in the presence of ATP.

The ε subunit according to the present invention may include the naturally-occurring amino acid sequence or any variant sequence having substitution, insertion, or deletion of one or more, such as one to five, amino acid(s) in the naturally-occurring sequence and the structure of the subunit change upon specifically binding to ATP. For example, the ε subunit according to the present invention may have substitution(s) so that it can inhibit the binding of a substance which interfere the change of the structure of the ε subunit upon binding to ATP. For example, the hydrophobic amino acid residue, such as Val9, Va142, Phe69 and Leu78 in SEQ. ID. NO. 1 or Va19, Va142, Phe67 and Leu78 in SEQ. ID. NO. 2, which is necessary for the interaction with γ subunit, another subunit of the ATP synthase may be substituted with a hydrophilic amino acid residue. As shown in SEQ ID NO. 3, the naturally-occurring sequence may be introduced with a mutation of R122K and/or RI 26K.

The fluorescence-labelled fusion protein according to the present invention is a fusion protein composed of two distinct fluorescent proteins and an ε subunit.

The two distinct fluorescent proteins in the fusion protein may be, but not limited to, any pair of known fluorescent proteins that can serve as the donor and acceptor for FRET. FRET is a process by which excitation energy is transferred from the donor molecule in an excited electronic state to the acceptor molecule when the molecules are within a certain distance each other. The FRET signal is generally detected by irradiating the excitation light to the donor molecule, and then measuring the fluorescence intensity(ies) emitted from the donor molecule and/or the acceptor molecule. When fluorescence emission from the donor is detected, the fluorescence emission decreases as the distance between the donor and acceptor molecules decreases because the acceptor absorbs the light, while the fluorescence emission increases with the distance between the donor and acceptor molecules increases. Conversely, when the fluorescence emission from the acceptor molecule is detected, the fluorescence emission increases with the distance between the molecules increases.

The fluorescence protein may be selected from those generally used for FRET. Particular examples include a fluorescent protein derived from *Aequorea victoria* such as a green fluorescent protein (GFP); an enhanced fluorescent protein genetically engineered by introducing a mutation into the GFP, such as a yellow fluorescent protein (YFP), a cyan fluorescent protein (CFP), and a blue fluorescent protein (BFP); a fluorescent protein from coral such as a red fluorescent protein (RFP) and an kusabira-orange protein (KO). In addition, the fluorescent proteins listed in Table 1 of Nature Methods 2012(9)10: 1005-1012 may be used.

A pair of fluorescent proteins as a donor and an acceptor for obtaining a FRET signal may include a CFP and a YFP, a BFP and a GFP, or a GFP and an RFP. Either one of the pair may be attached to the amino terminal moiety and the other to the carboxy terminal moiety of the ε-subunit. Commercially available fluorescent proteins may be used in the present invention, For example, a CFP is commercially available from Invitrogen, Inc., a YFP is from Invitrogen, Inc. or from Evrogen Inc. under the name of Phi-Yellow, a GFP is from Clontech Inc. under the name of EGFP and from Evrogen Inc. under the name of Tag-GFP, and an RFP is from Clontech Inc. under the name of DsRed2-monomer or from Evrogen Inc. under the name of HcRed-Tandem.

The non-human mammal according to the present invention may be obtained by incorporating a DNA encoding the fluorescence-labeled fusion protein as described above into the chromosome of the non-human mammal and expressing the fluorescence-labeled fusion protein in the non-human mammal.

The fluorescence-labeled fusion protein encoded by the DNA is preferably expressed under the control of a pronotor sequence that can function in the non-human mammal. The promoters may be a ß-actin promoter, a CMV promoter, or a CAG (CAGGS) promoter. In view of the expression rate, the especially preferable promoter is a CAG (CAGGS) promoter, The promoter may be stage-specific or tissue-specific.

A DNA construct encoding the fluorescence-labeled fusion protein may include a selection marker. The "selection marker" refers to a genetic element that confers a selectable phenotype on the cells to which the selection marker is introduced. The selection marker may generally be a gene that provides cells with biological properties including resistance to an agent that inhibits cell growth or kills cells. Particular examples of selection markers may include a Neo gene, a Hyg gene, a hisD gene, a Gpt gene and a Ble gene. Agents that are useful for selecting the introduced markers may include G418 for the Neo gene, hygromycin for the Hyg gene, histidinol for the hisD gene, 6-thioxanthine for the Gpt gene, and bleomycin for the Ble gene.

The DNA construct encoding the fluorescence-labeled fusion protein may preferably include additional sequences homologous to the target region on the chromosome when the endogenous target gene is replaced with the DNA construct by homologous recombination. The target region on the chromosome is preferably the Rosa26 locus.

The ROSA26 locus in mouse was discovered by Friedrich and Soriano in 1991 through a gene trapping experiment using embryonic-stem (ES) cells infected with retrovirus (Friedrich, G. and P. Soriano, Genes & Development, 1991 (5): 1513-1523). The ROSA26 locus has been widely used as a target region of homologous recombination in mouse ES cells for making transgenic mice (Kisseberth et al., Developmental Biology, 1999 (214): 128-138; MaoX et al., Proc. Natl. Acad. Sci. USA, 1999 (96): 5037-5042; Soriano, 1999 (cit); Awatramani et al., Nature Genetics, 2001 (29): 257-259; Mao X. et al., Blood, 2001 (97): 324-326; Possemato et al., Genesis, 2002 (32): 184-186; Mao, J., et al., Nucleic Acids Res, 2005 (33): e155; Yu et al., Proc. Natl, Acad, Sci, USA, 2005 (102); 8615-8620; International Application WO 99/53017, WO 02/098217, WO 03/020743, WO 2004/063381 and WO 2005/116070).

The DNA construct encoding the fluorescence-labeled fusion protein may include recognition sequences, such as Lox sequences, for a recombinase such as a Cre recombinase or a Flp recombinase. For example, the DNA construct may include a promoter sequence and a coding sequence of the fluorescence-labeled fusion protein, and further include a stop codon or a drug-resistant sequence between the promoter and coding sequences. When the stop codon and/or the drug resistant sequence is/are removed by the Cre recombinase, the prornotor sequence is operably linked to the coding sequence and the transcription of the coding sequence under the control of the promoter begins. Examples of Lox sequences may include loxP, lox71, lox66, lox511, lox2272, Vlox (VCre), and Slox (SCre). Alternatively, FRT sequences may be used as recognition sequences recognized by FLP.

A transgenic non-human mammal may be produced, for example, by a method comprising the following steps (a)-(g):

a) introducing a targeting vector comprising a DNA construct including the coding sequence of a fluorescence-labeled fusion protein into embryonic stem (ES) cells obtained from a non-human mammal;
b) selecting the ES cells that harbor the DNA construct integrated into the chromosome;
c) injecting the selected ES cells into fertilized eggs;
d) transferring the fertilized egg into the uterus or uterine tube of a pseudo pregnant female non-human mammal;
e) selecting germline chimeras from the offspring of the non-human animal;
f) mating the selected germline chimeras each other to give offspring and selecting an animal that carry the integrated DNA construct including the sequence encoding the fluorescence-labeled fusion protein; and
g) mating two animals selected in the step f) to give offspring and selecting a transgenic non-human mammal that carries the DNA construct integrated homozygously in both of the homologous chromosomes.

The procedures as above are described, for example, in Hogan et al., Manipulating the Mouse Embryo: A Laboratory Manual, Cold Spring Harbor Laboratory (1986), and U.S. Pat. Nos. 5,616,491 and 5,750,826.

A method for making the transgenic animals is described in detail.

ES cells can be obtained by culturing the embryos in vitro under an appropriate condition before the embryos are transplanted (Nature 1981 (292): 154-156; Nature 1984 (309): 255-258; Proc. Natl. Acad. Sci. USA 1986 (83): 9065-9069; and Nature 1986 (322): 445-448).

A targeting vector may be efficiently introduced into the ES cells via DNA transfection using a procedure known in the art such as electroporation, calcium phosphate co-precipitation, fusion of protoplasts or of spheroplasts, lipofection and DEAE-dextran-mediated transfection.

A foreign gene may be introduced into a non-human mammal via virus infection when a virus vector is used as a targeting vector. For example, adenovirus, retrovirus, and lentivirus may be used for the virus infection. Non-human developing embryos are cultured to the blastocyst stage in vitro. During the culture, the blastomeres are infected with virus (Proc. Natl. Acad. Sci. USA 1976 (73): 1260-1264). The transfection can be easily and efficiently achieved by culturing the blastomeres on a monolayer of cells that produce virus particles (EMBO 1987 (6): 383-388). Alternatively, virus infection may be achieved at the stage later than the blastocyst-stage. Virus or a cell that produces virus particles may be injected into the blastocoels (Nature (1982) 298: 623-628).

Also, a foreign gene may be introduced into the germ-line genome of an embryo via intrauterine viral infection at mid-pregnancy. Viral particles or Mitomycin C treated cells that produce virus particles may be microinjected into the fertilized eggs or around perivitelline cavum of the early embryo.

Other methods such as nuclear microinjection (U.S. Pat. No. 4,873,191); gene targeting in embryonic stem cells (Cell 56: 313-321 (1989)); electroporation of embryos (Mol Cell. Biol. 3: 1803-1814 (1983)); and sperm-mediated gene transfer (Cell 57: 717-723 (1989)) may be used.

ES cells transfected with a foreign gene of interest has been introduced in this way are injected into the blastocoel of embryos at the blastocyst stage. Then, the ES cells are incorporated into the embryo and the embryos become germ-line cells of the chimeric animal. When the gene transfection enables the genetic selection, transfected ES cells may be genetically selected to enrich the ES cells having the foreign gene before the injection into the blastocoel. Alternatively, a PCR method may be used to screen the ES cells containing the gene of interest. It is accordingly possible to improve transfection efficiencies.

The injected embryos are transferred to uterine tubes or uteruses of pseudo pregnant female animals to produce transgenic animals. Once a first-generation transgenic animal is produced, the first-generation transgenic animal may be mated or crossed with a homozoic or heterozoic animal to produce a specific group of animals. For example, a transgenic animal that is useful for assessing diseases and screening for therapeutic agents may be created by mating the transgenic animal mated with a non-human disease-model mammal.

Non-human disease-model animals may include an autism-model animal (e.g., Caps2 Δexon3, Sadakata, T. et al. PNAS 2012: www.pnas.org/content/early/2012/11/28/1210055109.full.pdf) and a heart disease-model animal. Heart disease-model animals may include model animals that mimic cardiac infarction conditions or hypoxic conditions.

Disease-model animals used in the present invention may further include, but are not limited to, a diabetic-model animal such as a db/db mouse and a cancer-model animal such as an animal with a p53/k-ras mutation.

The non-human transgenic mammal expressing the fluorescence-labeled fusion protein according to the present invention and the cell or the tissue obtained therefrom may be used to measure the level and the distribution of ATP and further to measure the time-dependent changes in the level and the distribution of ATP. ATP induces a structural change in the ε subunit of the ATP synthase in the fusion protein, thereby producing a FRET signal of fluorescence, which can be monitored with a fluorescent microscopy. Accordingly, the fluorescence-labeled fusion protein enables to monitor the presence of in vivo ATP with a fluorescent microscopy.

The non-human transgenic mammal according to the present invention, and the cells or the tissues obtained therefrom may be useful for screening for a cancer therapeutic agent. For example, candidate compounds are applied to the non-human transgenic mammal, the cells, or the tissue, and are screened for cancer-killing properties on the basis of the accurate measurement of the ATP level or the detection of changes in the ATP level. They may also be used for assessing drug safety. For example, hepatic cells may be used to precisely evaluate the effects such as toxicity and burden to liver of a drug on the basis of the measured changes in the ATP levels.

The non-human transgenic mammal according to the present invention, and the cell or the tissue obtained therefrom may be used for investigating or assessing various pathological conditions, estimating the efficacy of a drug, or drug screening. For example, they may be used to screen therapeutic candidate compounds for a disease which changes the energy metabolism status in individual cells and to assess the drug efficacy of a therapeutic candidate compound. Further, cells or tissue of the heart may be used to screen therapeutic candidate compounds for treating a heart disease and to assess the efficacy of a therapeutic candidate compound on the heart. In addition, they may be used to screen therapeutic candidate compounds for treating diseases induced by excessive levels of ATP when candidate compounds are administered to them and then assessed for the effect of the compounds to reduce the ATP level. Alternatively, therapeutic candidate compounds may be screened for diseases induced by a low ATP level when the candidate compounds are assessed for the effect of the compounds to increase the ATP level.

Compounds, which are used as therapeutic candidates in the assessment and screening method, may include synthetic or natural-occurring compounds with low or high molecular weight, metal-containing compounds, carbohydrates, peptides, proteins, peptidomimetics, glycoproteins, lipoproteins, nucleic acids, and antibodies. A library including a large number of natural-occurring or synthetic compounds may also be used.

The non-human transgenic mammal according to the present invention, and the cells or the tissue obtained therefrom enable to investigate time-dependent changes in the level and the distribution of ATP. In the cell or organ whose energy metabolism changes in response to exercise in a time-dependent manner, abnormal exercise or abnormal function of the cell or organ may be detected as the abnormal time-dependent change of the ATP levels and distributions. Accordingly the non-human transgenic mammal, the cells or the tissue may be used as tools for developing new therapeutic or treatment methods. The information of the changes in the level and the distribution of ATP in the organ enable to machinery reproduce the movement of the organ, For example, the information of the changes of the ATP distribution in the muscles enables a machine to mimic the movement of the body, for example, enable a machine to reproduce the movement of walking.

In addition, the measurement of the ATP levels in a cell or tissue of the muscles enables to assess the recovery of the muscles after exercising. Accordingly the present invention may be used not only for investigating muscle-relating diseases but also for developing an exercise and fitness equipment, a functional food or a muscle-boosting product.

Cells obtained from the non-human mammal according to the present invention may be used to quantify the ATP level.

Measurement conditions described below may be useful. Test materials may include a composition containing ATP, such as a solution containing ATP, a biological sample such as a cell, an extract of a biological sample. Lysis buffers may be, but is not limited to, a buffer whose pH is optimal for the fluorescent protein to emit fluorescence. Specifically, when YFP is used as a fluorescent protein, a buffer solution with pH of more than 7 is preferable because an acidic condition reduces the emission rate of YFP fluorescence. Reaction temperatures may be a temperature that induces a structural change in the fluorescence-labeled fusion protein. For example, measurements can be carried out at 37±1° C. or 25±1° C. Reaction time may be appropriately selected unless the protein of interest does not degrade, and may preferably be more than one minute. Additives may be appropriately added to the reaction solution. For example, 0.05% surfactant (Triton X-100) or 1mg/mL bovine serum albumin (BSA) may be added as a stabilization agent. A chelating agent such as EDTA or EGTA may be added to avoid the influence of magnesium which is possibly included in the test sample.

Fluorescence spectrum of the test sample after the reaction may be measured with a fluorometer. The donor is exited with the suitable wavelength and the fluorescence intensity of each fluorescent protein is measured at the wavelength where each fluorescent protein alone provides individual peak. A FRET signal can be measured by calculating the ratio of the measured fluorescent intensities. Solutions containing ATP at several concentrations are prepared and the ratios of measured fluorescent intensities are calculated to make a calibration curve. The ATP level in a test sample may be estimated from the measured FRET signal with the calibration curve.

EXAMPLES

The present invention will be described in more detail with reference to the following examples. The present invention however is not limited to the examples.

Targeting vectors including a cDNA sequence encoding GO-ATeam (GO-ATeam1 and GO-ATeam2) to integrate the respective cDNA sequence into the ROSA26 locus of the mouse were constructed and used to generate a transgenic mouse for visualization of ATP (FIG. 1). The targeting vector was constructed by inserting the STOP sequence flanked by the LoxP sequences so that the GO-ATeam was under the control of the GAGGS promoter sequence and was expressed at the place where and at the time after Cre was expressed.

Preparation of the Targeting Vectors

A pBlueScript vector gifted from Dr. Katsuaki Hoshino was used. The pBlueScript vector contained, in order, mouse ROSA26 5' arm of 1080 bp (Ch6 113076036-113077116), Splice acceptor, and bovine growth hormone poly A (BGH pA) followed by CAGGS promoter, LoxP, pA, Neo (inverted), MC1 (inverted), STOP sequence including SV40pA sequence, LoxP sequence and BGH pA. Then, ROSA26 3' arm of 4267bp (ch6 114900586-114904926) was connected thereto followed by PGK promoter, a DT-A, and a BGH pA. The pBlueScript vector used herein is referred hereinafter to as ROSA26-CAG-STOP vector.

The pBS-APS vector was obtained by introducing Asc I, Pme I and Swa I at both ends of the multi-cloning site (MCS) of the pBlueScript vector in order from the MCS. The pBS-APS vector was digested with Pme I, and was treated with T4 DNA polymerase. A fragment including the STOP sequence 149 bp and the LoxP sequence, which were obtained from the ROSA26-CAG-STOP vector, followed by the stuffer fragment from pEF-BOS vector (Nucleic Acids Res. 1990 Sep 11; 18 (17): 5322.) and G-CSF pA sequence, and further the ROSA26 3' arm sequence 49 bp (ch6 114904549-114904597) was ligated into the digested pBS-APS vector. The ligated vector was used in the following procedures and is referred to as liMOG-GA_pBS-APS vector.

cDNAs obtained from pcDNA vectors containing GP-ATeam1 and GO-ATeam2 respectively gifted from Dr. Hiromi IMAMURA were used. The pcDNA vector was cleaved with Nhe I and Hind III. The Hind III site of the fragment was treated with T4 DNA polymerase.

The liMOG-GA_pBS-APS vector was digested by Nhe I and Xba I. The digested vector was treated with T4 DNA polymerase to form blunt ends at the cleaved Xba I site.

The fragment from the pcDNA vector and the cleaved liMOG-GA_pBS-APS vector were ligated to obtain a vector GO-ATeam 1_liMOG-GA and GO-ATeam 2_iMOG-GA.

The GO-ATeam 1_iMOG-GA and GO-ATeam 2_iMOG-GA vectors were digested with Swa I to obtain cDNA fragments. The ROSA26-CAG-STOP vector was digested with Asc I and Nru I, and the digested vectors were treated with T4 DNA polymerase. The obtained fragments containing the cDNA were ligated to the cleaved vector with the GeneArt® kit (Invitrogen) to obtain the targeting vectors.

The abbreviations of GO-Ateam 1 and GO-Ateam 2 stand for:

Ateam: Adenosine 5'-Triphosphate indicator based on Epsilon subunit for Analytical Measurement.

GO-Ateam: GFP- and OFP-based ATeam.

GO-Ateam 1: A construct encoding a fusion protein that has the ε-subunit of bacillus subtilis F0F1-ATP synthase (SEQ ID NO: 2), GFP (cp173-mEGFP) inserted into the N terminus of the ε-subunit and an OFP (mKOK) inserted into the C terminus. The construct does not include any signal sequence and the fusion protein is expressed in the cytosol.

GO-Ateam 2: A construct encoding the same fusion protein as GO-Ateam 1 except that the ε-subunit has a mutation R122K/R126K (SEQ ID NO: 3). The construct does not include any signal sequence and the fusion protein is expressed in cytosol.

REFERENCES

Imamura et al., Pro N.A.S. 2009 (106): 1 5651-15656

Nakano et al., ACS Chem. Biol. 2011 (6): 709-715

Waldeck-Weiermair et al., PLoS ONE 2012 (7)9: e45917

WO 2008/117792

Production of Chimeric Mouse

The above produced targeting vector was linearized with AsiS I. The linearized vector was introduced into ES cells (C57/BL6x129 hybrid) according to a conventional method. The ES cells were screened for the presence of neomycin resistance gene by PCR or by Southern Blotting to obtain ES cells transfected in the manner that the GO-ATeam is expressed only when the Cre recombinase is expressed. ES cells constantly expressing the GO-ATeam were obtained by introducing a CMV-Cre vector into thus obtained ES cells.

The above obtained ES cell was fused with morulae of an ICR mouse by means of the aggregation method and the fused cell was transferred to the uteruses of a pseudo pregnant female ICR mouse to produce chimeric mouse that expresses GO-ATeam 1 or 2 in the cytosol.

Measurement of ATP

From day 13 embryos of the above mice expressing GO-ATeam 1 or 2 for visualization of ATP, MEF cells were obtained and cultured.

Figure 2:
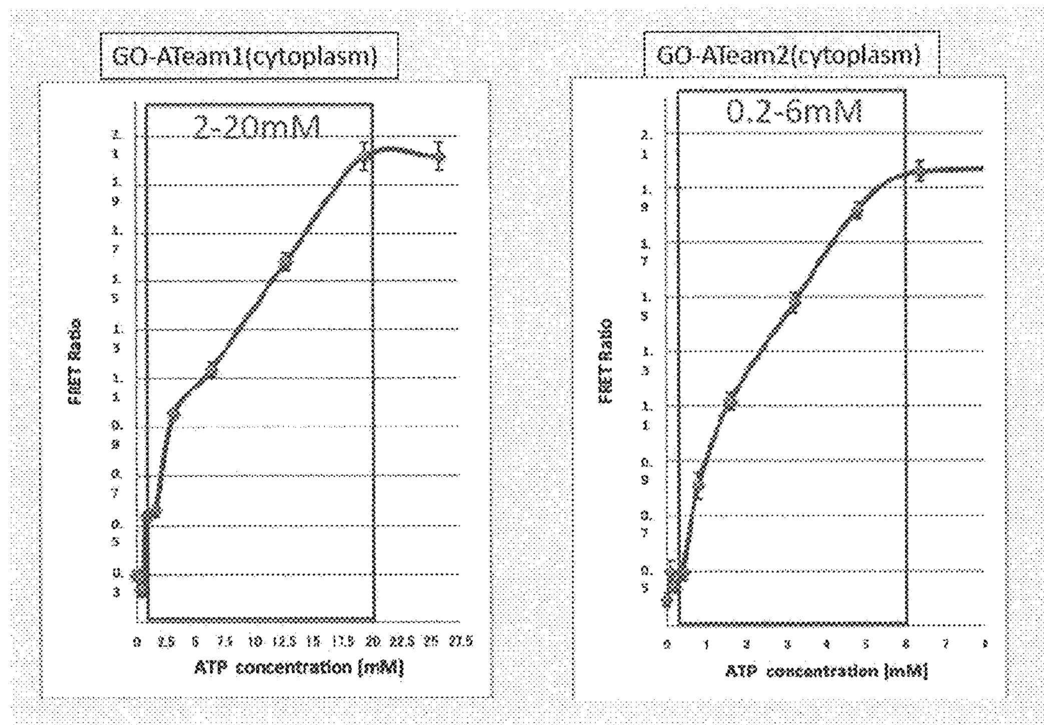
FIG. 2 provides graphs showing the ratio of ATP concentration to the FRET.
Figure 3:
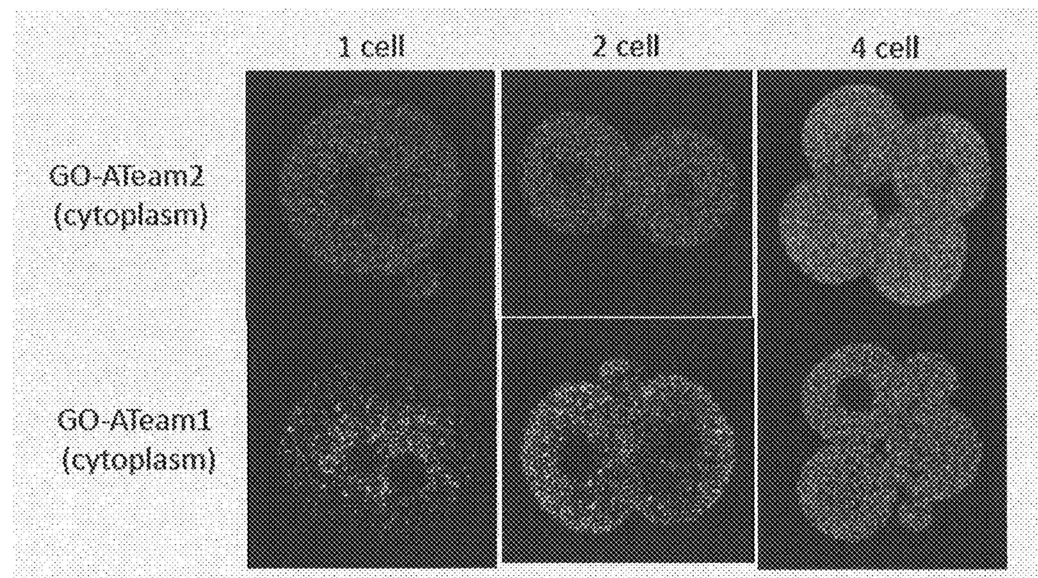
FIG. 3 provides fluorescence microscope photographs showing the distribution patterns of ATP in mouse embryos expressing GO-ATeam 1 or 2 at the 1st-cell stage, 2nd-cell stage and 4th-cell stage.
Figure 4:
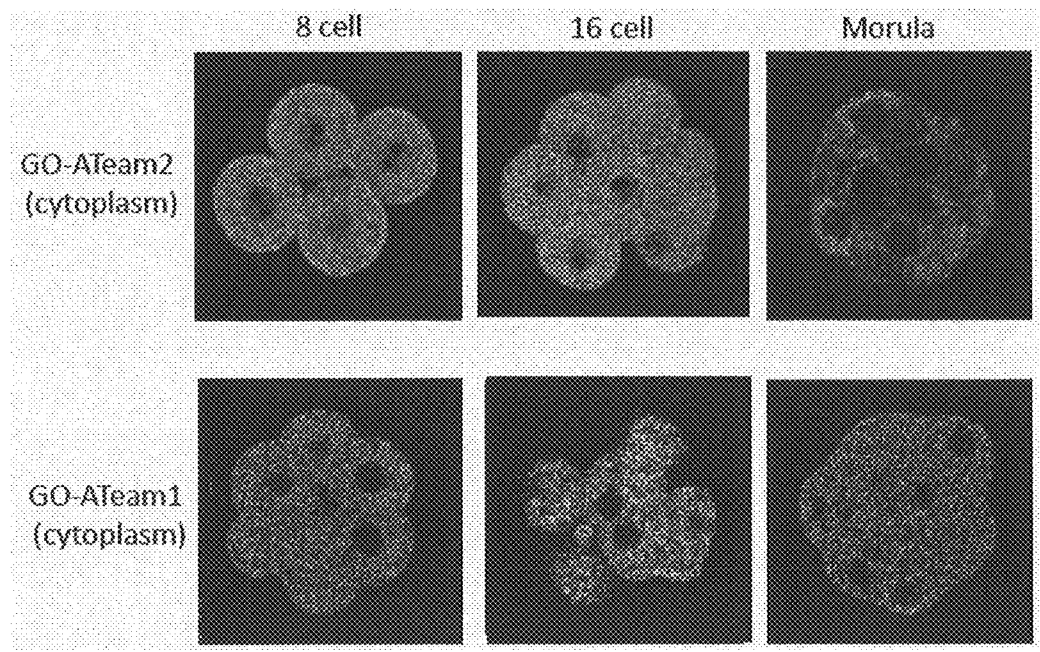
FIG. 4 provides fluorescence microscope photographs showing the distribution patterns of ATP in mouse embryos expressing GO-ATeam 1 or 2 at the 8-cell stage, 16-cell stage and morula stage.
Figure 5:
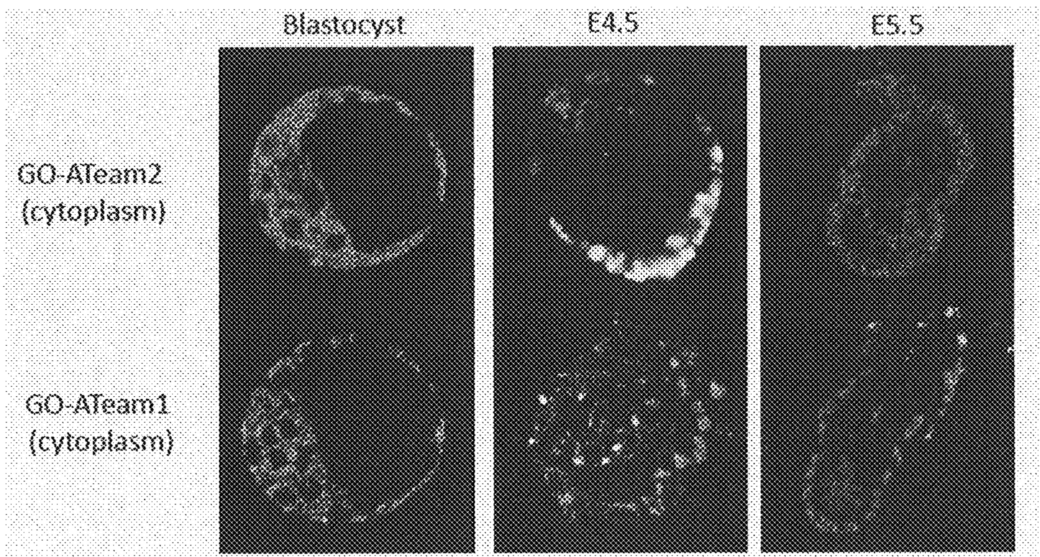
FIG. 5 provides fluorescence microscope photographs showing the distribution of ATP in the mouse embryo expressing GO-ATeam 1 or 2, at the blastocyst stage, E4.5 stage and E5.5 stage.
Figure 6:
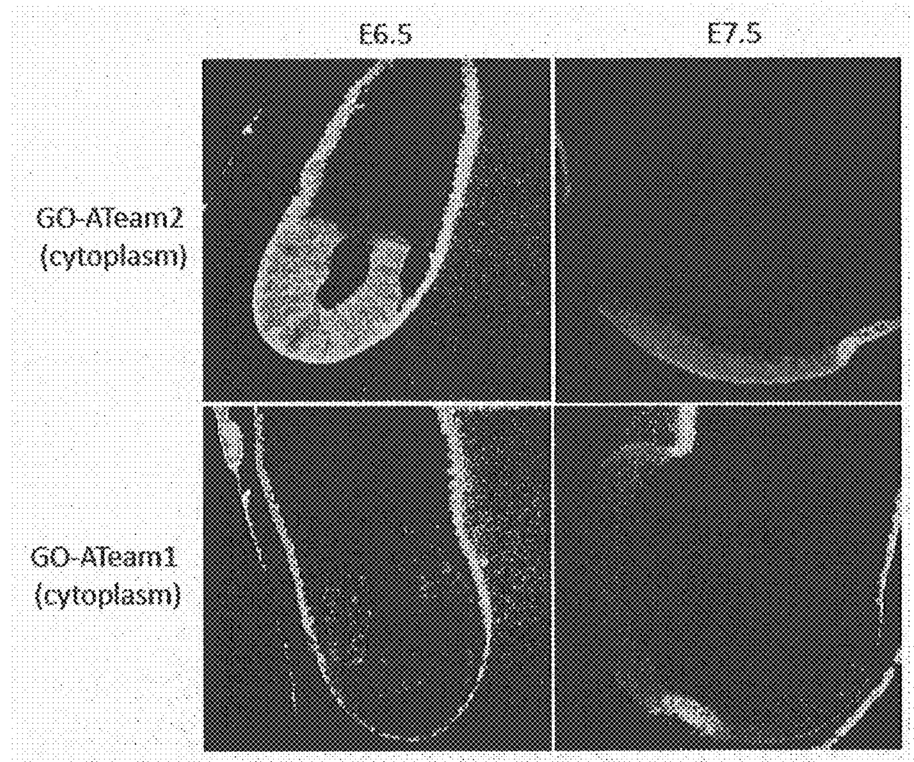
FIG. 6 provides fluorescence microscope photographs showing the distribution of ATP in the mouse embryo expressing GO-ATeam 1 or 2, at the E6.5 stage and E7.5 stage.

The MEF cells were passaged four times and then seeded on a coated glass dish. The MEF cells were washed with a Permilization buffer (140 mM KCl, 6 mM NaCl, 0.1 mM EGTA, and 10 mM HEPES, pH7.4) and treated with Permilization buffer supplemented with 50 μg/ml α-Hemolycin (Sigma cat# H9395) at 37° C. for 30 minutes. Then, the treated cells were conditioned with calibration buffer (140 mM KCl, 6 mM NaCl, 0.5 mM $MgCl_2$, 10 mM HEPES, pH7.4) supplemented with 0-30mM of MgATP. Fluorescence image of the cells in the presence of each concentration of ATP was taken using a confocal microscope equipped with a laser configuration (488 nm) with DM405/488 as an excitation DM. Fluorescence signals emitted from GFP and from Kusabira orange fluorescent protein were divided by LM01-552 dichroic mirror with the shorter wavelengths directed to pass through BA505-540 bandpass filter and the longer wavelengths directed to pass through BA575-675 bandpass filter, and received by individual detectors. The fluorescence images were analyzed with Metamorph software to calculate the FRET ratios. The calculated FRET ratios are plotted against the concentrations of ATP (FIG. 2).

A linear increase in FRET ratio of GO-ATeam 1 was observed with increasing ATP concentration ranging from 2 to 20 mM. A linear increase in FRET ratio of GO-ATeam 2 was observed with increasing ATP concentration ranging from 0.2 to 6 mM. The measurement errors were within 4.5 percent. It is indicated that the ATP level in a range of 2 to 20 mM or 0.2 to 6 mM can be quantitatively measured in a mouse expressing GO-ATeam 1 or 2.

In vivo Imaging of ATP Levels

Fertilized eggs were obtained by mating a female mouse expressing either GO-ATeam 1 or 2 with a wild-type male mouse. The eggs were collected in DEME (Sigma) supplemented with 10% FCS. The collected eggs were cultured in M2 medium (Sigma) in an atmosphere of 5% $CO_2$ at 37° C. for three days after fertilization. Fluorescence images of the cells were taken in DEME (phenol red free) in an atmosphere of 5% $CO_2$ at 37° C. according to the procedure described above. After four days from fertilization, the cells were cultured in DMEM (Sigma) supplemented with 50% rat serum instead of the M2 medium. FRET ratios were measured according to the procedures described above. These results are shown in FIGS. 3-6.

ATP levels were measured in the fertilized cells at each stage. The distribution pattern of ATP in the cytosol differed at each stage of the cells. The ATP levels observed near nuclear were relatively low as compared to those observed in the other regions at the 1st-cell stage. At the 4th-cell stage, ATP levels near the contacting surfaces of the blastomeres were relatively low as compared to those in the other regions. It was found that the ATP level in embryonic ectoderm increased in the day 6.5 embryo as compared to the ATP level in the 5.5 day embryo. It was also found that the ATP level was enhanced in the node of the day 7.5 embryo.

The ATP levels measured in the mouse embryos with the FRET assay corresponded to the ATP levels measured with a luciferase assay.

ATP Distribution in vivo Adult Mouse

Figure 7:
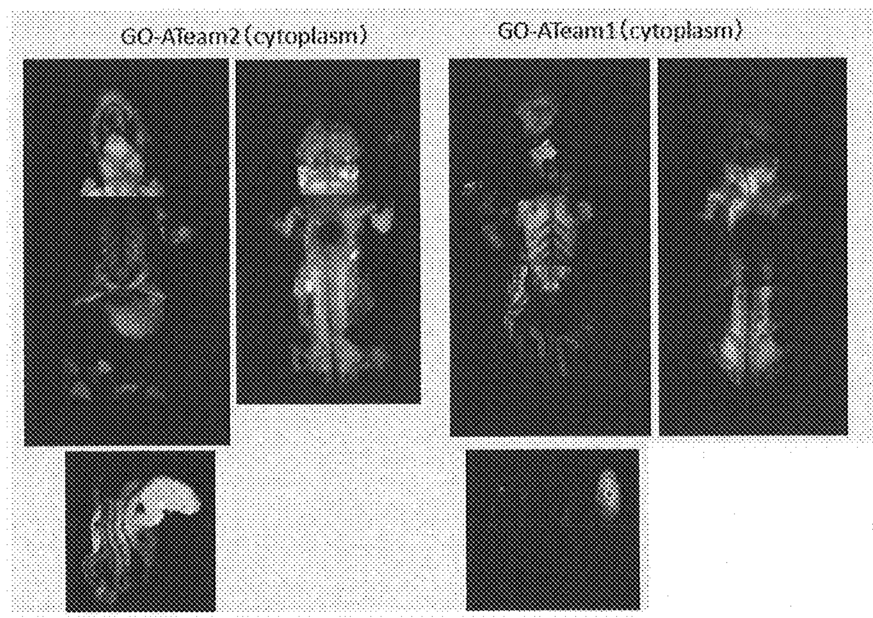
FIG. 7 provides fluorescence microscope photographs showing the distribution of ATP in organs of neonatal mice expressing GO-ATeam 1 or 2.
Figure 8:
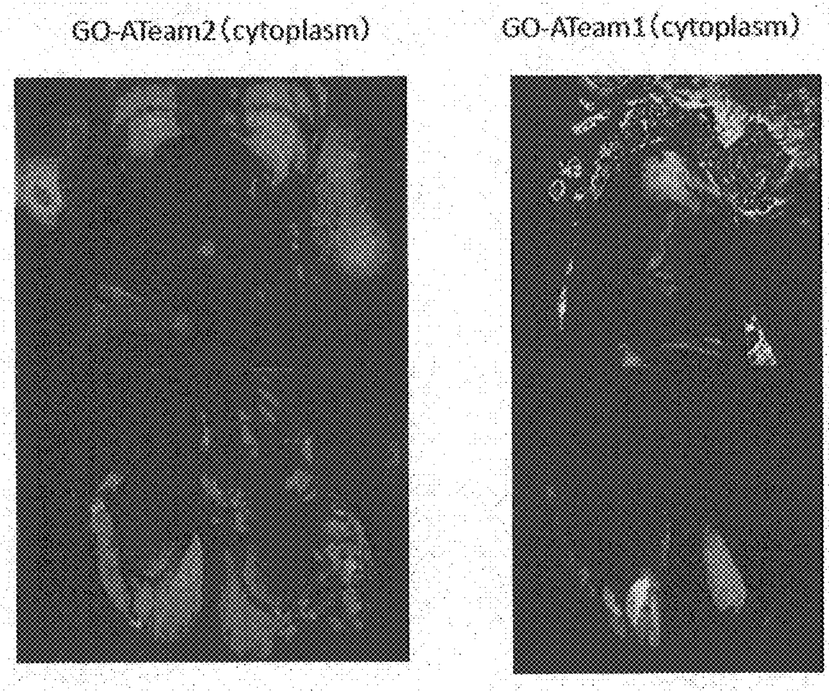
FIG. 8 provides fluorescence microscope photographs showing the distribution of ATP in organs of 12-month old mice expressing GO-ATeam 1 or 2.

A neonatal infant mouse and an adult mouse were subjected to throactomy under anesthetization gas and in vivo fluorescent images were obtained. The head of the mouse was removed from the body and acute brain slices of about 200 nm in thickness were prepared. Fluorescent images of the slices of the mouse brains were obtained. Imaging was carried out with a fluorescent microscopy (M165 FC from Leica, ltd.) equipped with a GFP3 filter (excitation wavelength ST470/40 nm and absorption wavelength ET525/50nm) and a GFP/OFP filter (excitation wavelength ET470/40 and absorption wavelength ET585/40). The fluorescent images were analyzed with Metamorph software to calculate FRET ratios. FIGS. 7 and 8 show these results. Relatively high ATP levels were observed in the muscle and heart in the living adult mice where the ATP levels had been reported being high based on the measurement using a luciferase assay.

Figure 9:
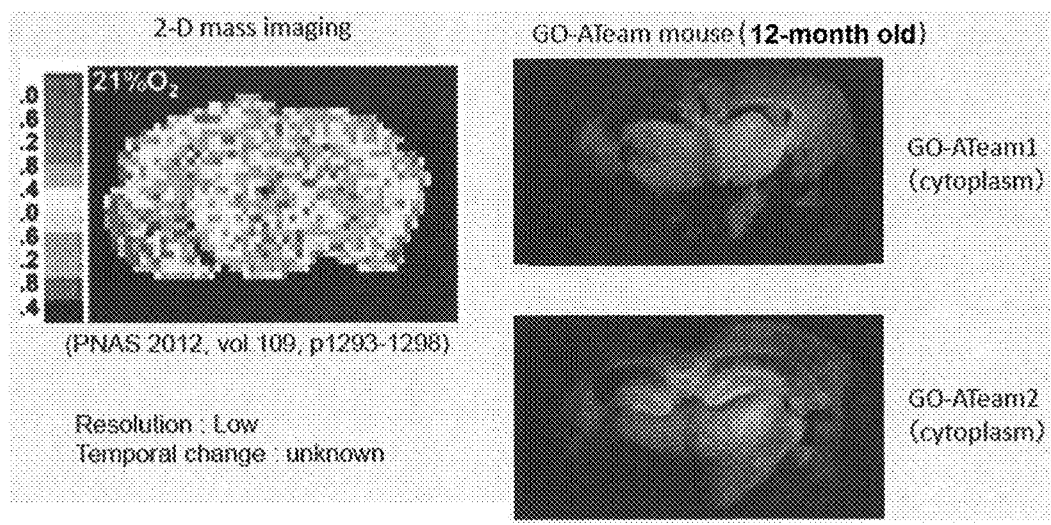
FIG. 9 provides fluorescence microscope photographs (right side) showing the distribution of ATP in the brain of 12-month old mice expressing GO-ATeam 1 or 2. The 2D mass-imaging photograph on the left side is a reference.

Fluorescent images were taken from the brain of a 12-month old adult mouse (FIG. 9). It was found that the time-dependent ATP levels in the brain of GO-Aterm knock-in mouse could be measured at higher resolution by using the FRET assay as compared to the mass spectrometry imaging assay.

According to the above, the ATP level could be measured at several portions of organs and the brain. The ATP levels measured by using the FRET assay in the transgenic mouse corresponded to the previously-reported ATP levels which were measured with a luciferase assay or an imaging mass spectroscopy. Conventional methods to measure the ATP level require hundreds of cells while the present method enables to measure the ATP level in a single cell or a subcellular level.

Figure 10:
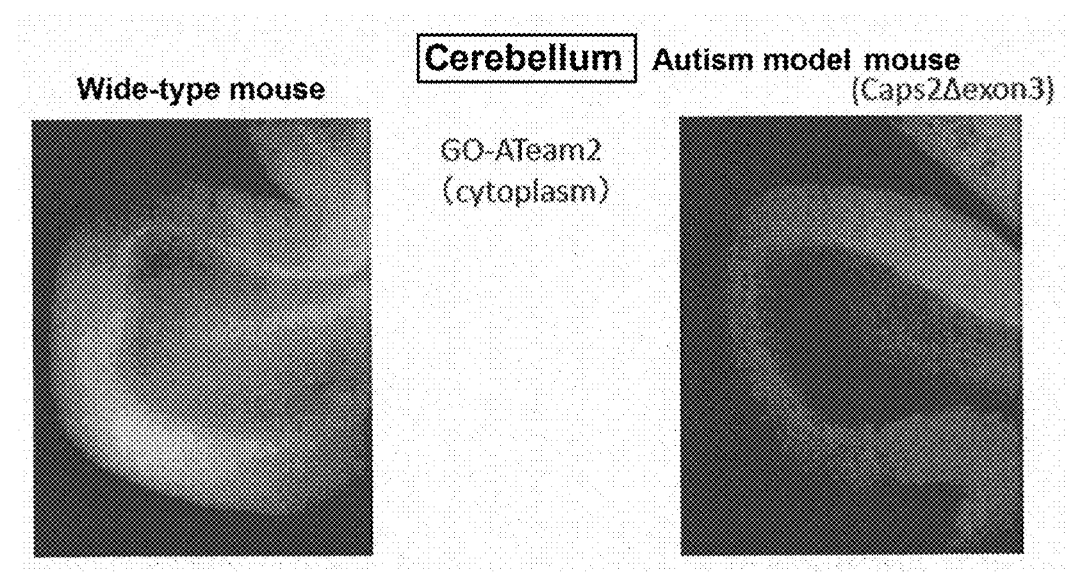
FIG. 10 provides fluorescence microscope photographs showing the distribution of ATP in the cerebellum of a mouse produced by mating a GO-ATeam 2 expressing mouse and an autism model mouse (Caps2Δexon3) and of a GO-ATeam 2 expressing mouse (wild type mouse).
Figure 11:
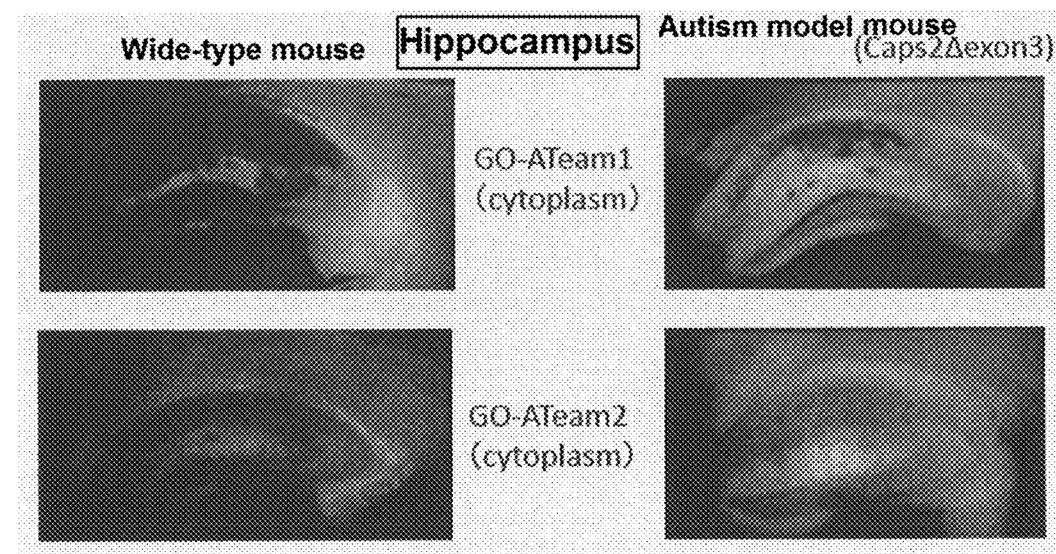
FIG. 11 provides fluorescence microscope photographs showing distribution of ATP in the hippocampus of a mouse produced by mating a GO-ATeam 1 or GO-ATeam 2 expressing mouse with an autism model mouse (Caps2Δexon3).; and of a GO-ATeam 1 or GO-ATeam 2 expressing mouse (wiled type).

Next, a transgenic mouse expressing GO-ATeam 1 or 2 was mated with the autism model mouse having abnormal cerebellum morphology and BDNF localization (Caps2Δexon3; Sadakata, T. et al., PNAS 2012) to produce a GO-ATeam 1 or 2-expressing autism model-transgenic mouse. The autism model-transgenic mouse was used to monitor the ATP level. Fluorescence images of the cerebellum in the transgenic mouse and that in the wild-type mouse are shown in FIG. 10. Enhanced ATP level was confirmed in the cerebellum of the autism model transgenic mouse. Fluorescence images of the hippocampus in the transgenic and the wild type mice were compared. As shown in FIG. 11, the ATP levels were low in the neuronal cell bodies and were high in the neuron dendrites in the hippocampus of the wild-type mouse while the ATP localization shown in the wild type mouse disappeared in the autism model transgenic mouse.

Figure 12:
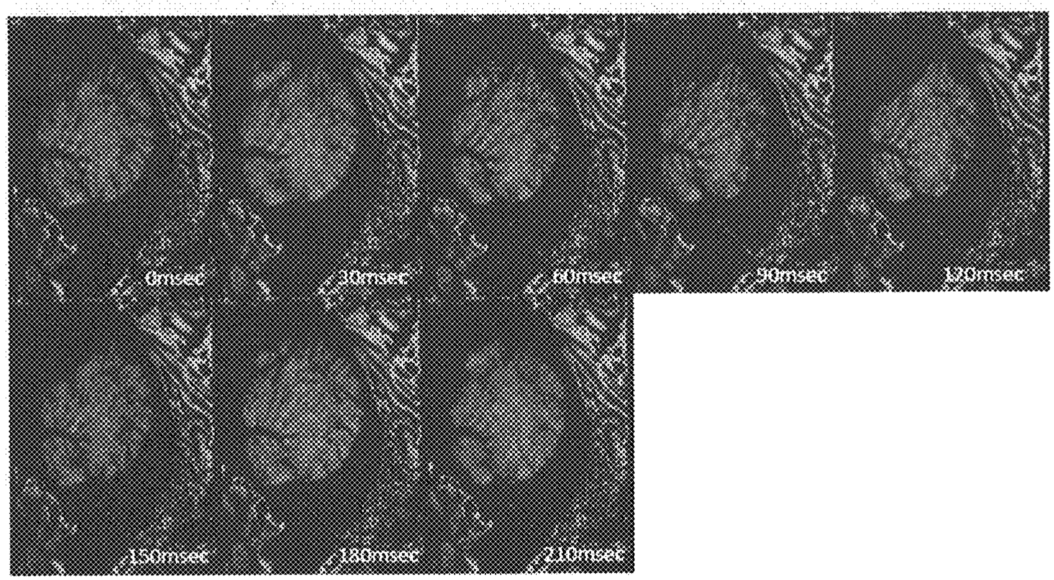
FIG. 12 provides fluorescence microscope photographs showing time-dependent distribution of ATP in the heart of a GO-ATeam 2-expressing mouse under a normal condition.

Next, time-dependent changes in the ATP level were measured in the heart in the transgenic mice expressing GO-ATeam 2 under a normal condition, a hypoxic condition, or a cardiac infarction condition. Changes of the heartbeat (about 5 beats per sec) as well as of the level and the distribution of ATP were observed under the normal condition (FIG. 12). The results suggest that heart diseases such as myocardial infarction and cardiac malformation may be investigated or quantified from the perspective of physiological function.

Figure 13:
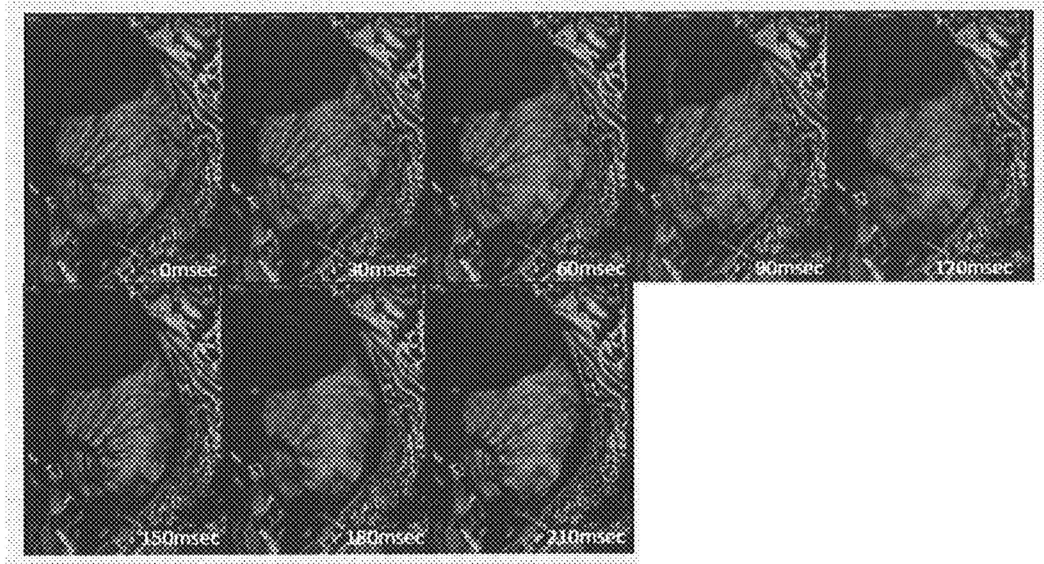
FIG. 13 provides fluorescence microscope photographs showing time-dependent distribution of ATP in the heart of a GO-ATeam 2-expressing mouse under a hypoxic condition.

FIG. 13 shows the results obtained under the hypoxic condition induced in a mouse controlled under an artificial respirator by ceasing the artificial respirator. The obtained fluorescent images indicate that the changes in the ATP level observed in the atrium under the normal condition disappeared in the atrium under the hypoxic condition. The changes in the ATP level were attenuated in the heart ventricle.

Figure 14:
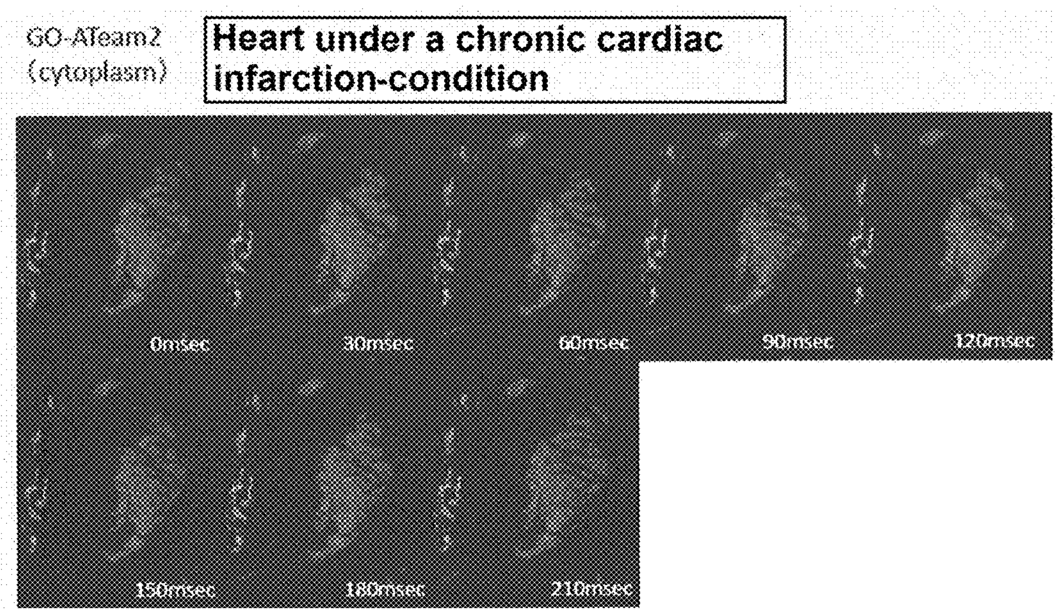
FIG. 14 provides fluorescence microscope photographs showing time-dependent distribution of ATP in the heart of a GO-ATeam 2-expressing mouse under a chronic cardiac-infarction condition.

FIG. 14 shows the results obtained in the heart on 5 days after the cardiac infarction induced by the coronary artery ligation. The obtained fluorescent images indicate that the ATP level at the infarction area on the heart ventricle decreased in the infarction model mouse. In the areas other than the infarction area on the heart ventricle increased ATP level was observed in some areas while decreased ATP level was observed in other areas as compared to a normal mouse.

Figure 15:
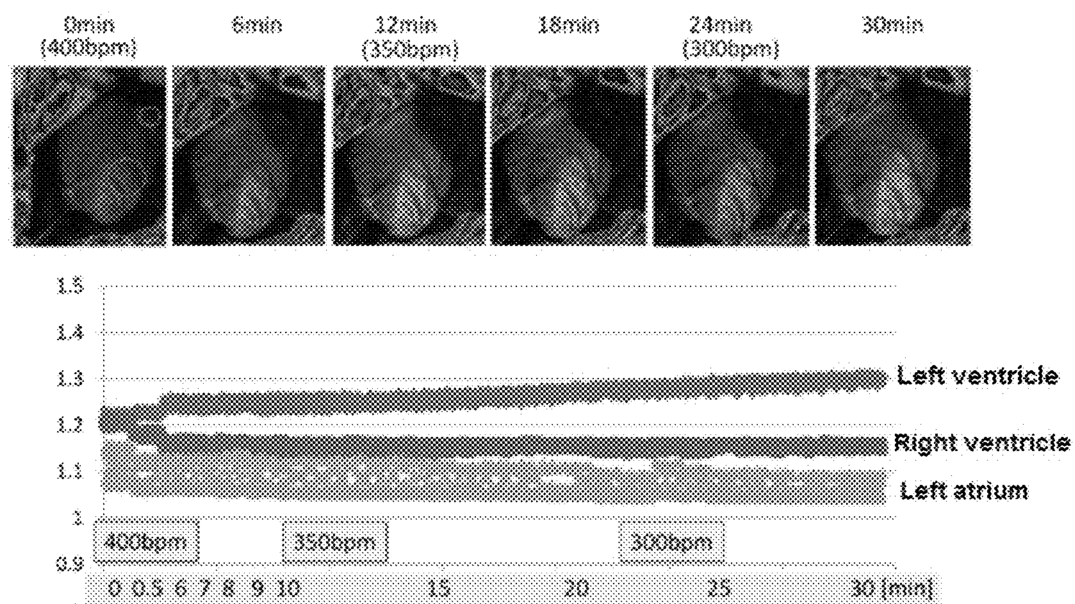
FIG. 15 provides fluorescence microscope photographs showing time-dependent distribution of ATP in the heart in a GO-ATeam 2-expressing mouse to which a β blocker was administered to decrease the heart rate, and a graph showing time-dependent ATP levels in each atrium and ventricle. The vertical axis of the graph indicates the relative value of the ATP level.

Next, the transgenic mouse expressing GO-ATeam 2 was anesthetized and connected to a ventilator. Propranolol, a β-blocker, was infused to the transgenic mouse through the carotid artery at a dose of 0.1 μg/kg per minute to decrease the heartbeat. The ATP levels on the right and left ventricles and left atrium of the hart in the transgenic mouse were monitored. Results are shown in FIG. 15. According to the results, the effect of the β-blocker, a heartbeat decreasing agent, was successfully traced on each part of the heart including ventricle and atrium, before and after the decrease of the heartbeat.

Figure 16:
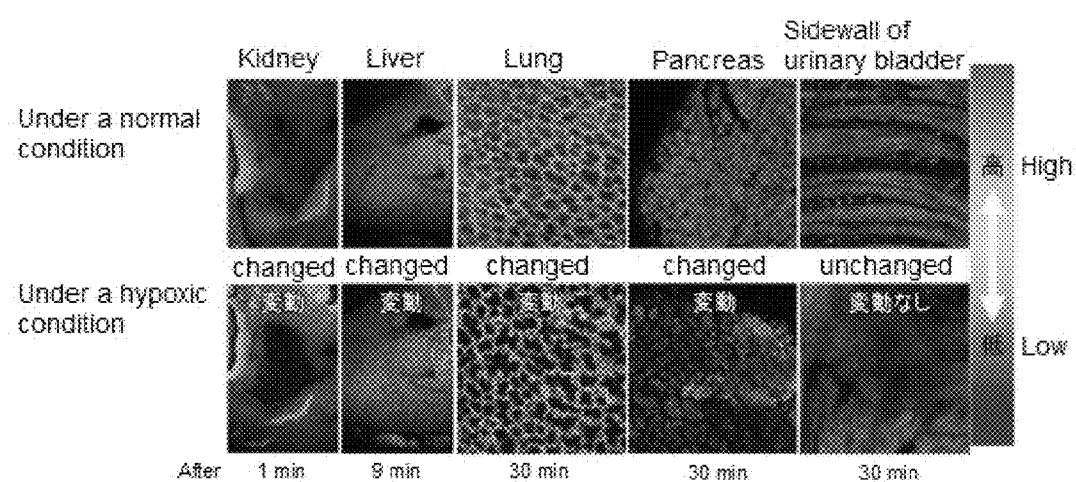
FIG. 16 provides fluorescence microscope photographs showing distribution of ATP in each organ of GO-ATeam 2-expressing mice under a normal condition and under a hypoxic condition.

Organs of the transgenic mouse expressing GO-ATeam 2 were placed in a hypoxic condition of a mixed gas of 95% nitrogen and 5% carbon dioxide. Time-dependent changes in the ATP level were monitored on each organ under the hypoxic condition and compared to the ATP levels in the corresponding organs under the normal condition. Results are shown in FIG. 16. The results indicate that monitoring the change of ATP levels enabled to quantify the change of the cellular activities in all observed organs.

Figure 17:
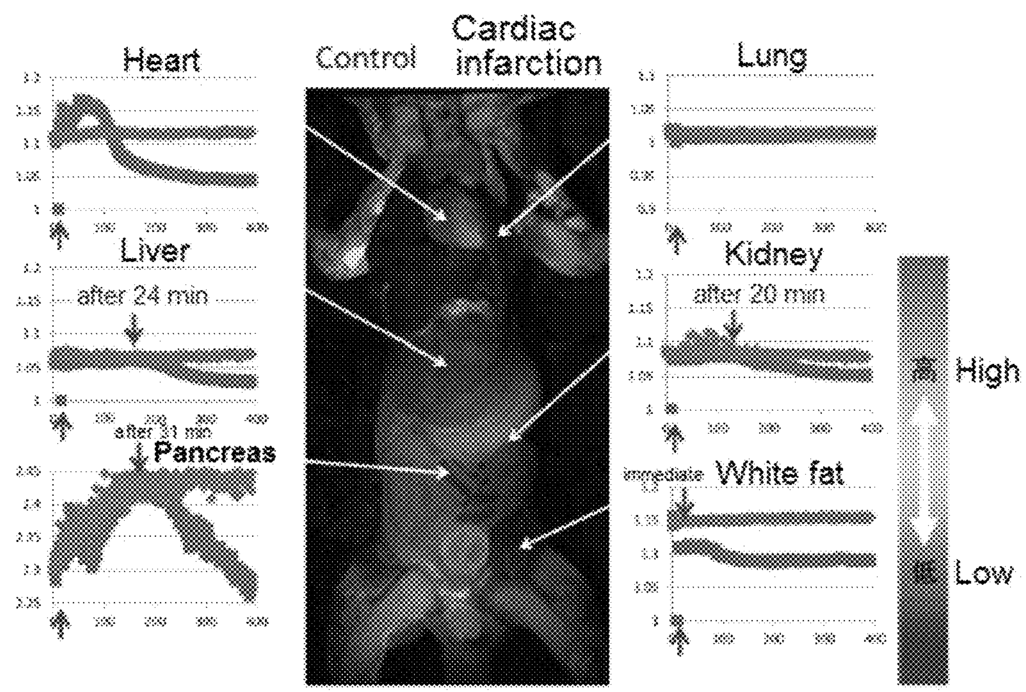
FIG. 17 provides scatter graphs that compare the time-dependent ATP levels in a GO-ATeam 2-expressing transgenic mouse treated to mimic a cardiac infarction condition (shown in red) to those in a GO-ATeam 2-expressing transgenic mouse which was treated with sham surgery as a control (shown in blue), The vertical axes of the graphs indicate the relative value of the ATP level. The horizontal axes indicate the time after the treatments in units of ten seconds. For example, the indicated scale in the horizontal axis is one hundred which is equal to one thousand seconds. The fluorescence microscope photograph in the middle shows the distributions of ATP in organs of the GO-ATeam 2-expressing mouse at zero second (control).

The transgenic mouse expressing GO-ATeam 2 was connected to a ventilator and the left anterior ramus descendens was ligated to mimic acute ischemia (cardiac infarction). Time-dependent changes in the ATP level were monitored on several organs and compared to the corresponding organs in the control transgenic mouse expressing GO-ATeam 2 that received sham surgery. Results are shown in FIG. 17. The arrows at zero second in the figures indicate the timing when the treatment of cardiac infarction was given to the transgenic mouse. Abnormal changes in the ATP level were observed on the liver after 24 minutes of the treatment, on pancreas after 31 minutes of the treatment, on kidney after 20 minutes of the treatment, and on white fat immediately after the treatment. These results indicate that the changes of the ATP level occurred at different time points on organs and that monitoring changes in the ATP level on each organ enables to assess the condition of the organ or cells when cardiac infarction occurs. Accordingly, monitoring changes in the ATP level on each and every part of body enables to access the pharmacological and toxic effects on the whole body.

Figure 18:
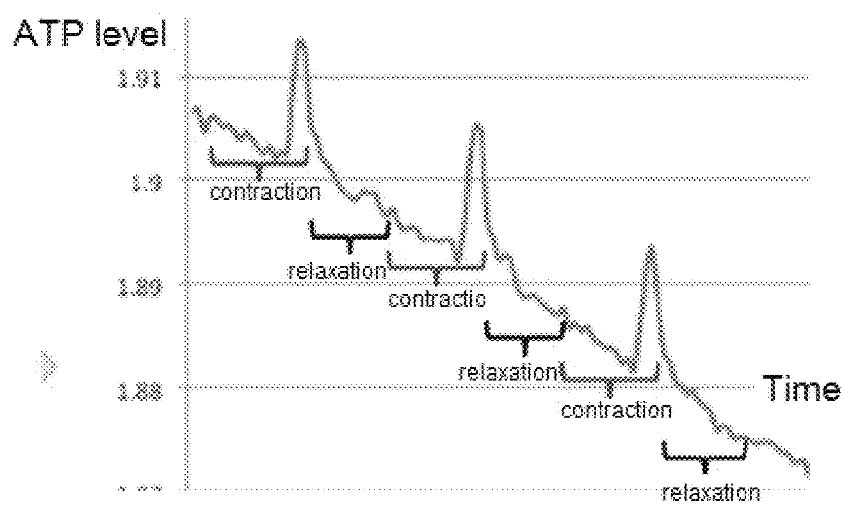
FIG. 18 is a line graph showing time-dependent changes of the ATP level associated with a contraction-relaxation cycle that was induced by electrical stimulation applied to cardiac muscle cells isolated from an adult GO-ATeam 2-expressing transgenic mouse. The vertical axis of the graph indicates the relative value of ATP level. The horizontal axis indicates time.

Next, myocardial cells were isolated from the heart of the transgenic mouse expressing GO-ATeam 2. Electrical pulses to induce muscle contraction were applied to the isolated myocardial cells and time-dependent changes in the ATP level were monitored. Result is shown in FIG. 18. The result suggests that the dynamic changes of the ATP level in a matured cardiac muscle cell can be monitored. The ATP level rapidly increased at around the end of the muscle contraction periods, indicating that ADP molecules were released from myosin and spread in the cytosol where ADP molecules were combined with phosphate ions derived from creatine phosphate. Then, ATP level in the cytosol gradually decreased as the muscle contracted. This indicates that ATP molecules started to bind to myosin.

Figure 19:
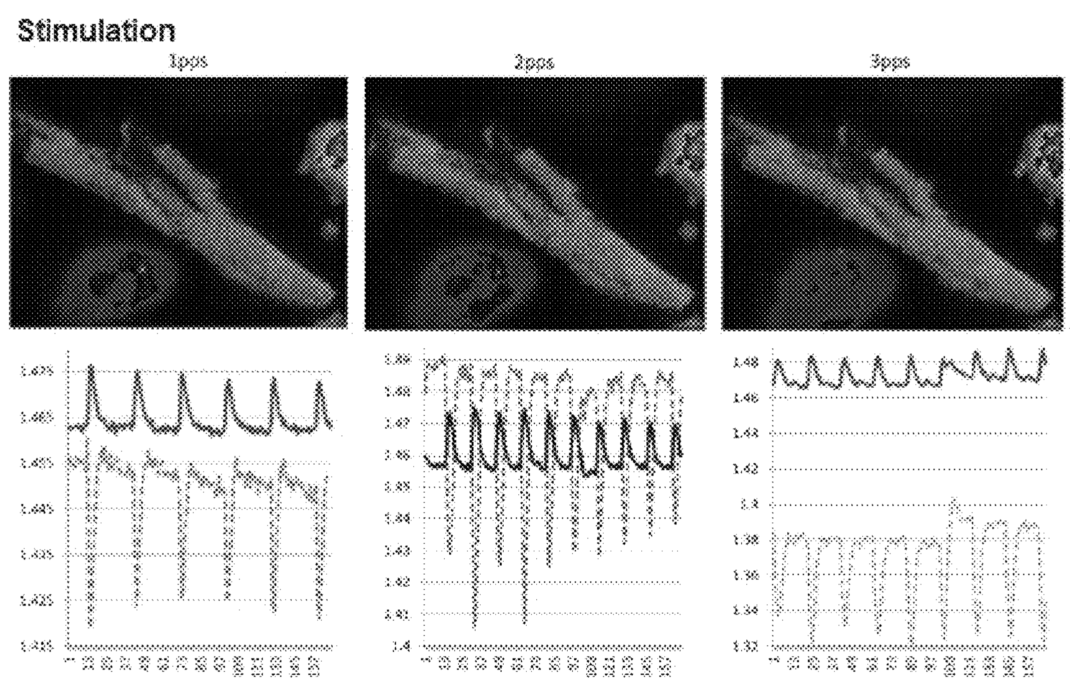
FIG. 19 includes fluorescence microscope photographs (upper panels) and line graphs (lower panels). The line graphs show time-dependent changes in the ATP level (solid lines) and in the area of a cardiac muscle cell (dashed lines) which was isolated from a GO-ATeam 2-expressing transgenic mouse and to which electrical stimulation was applied to induce a contractile motion. For the vertical axis of the graphs, the solid lines indicate the ATP level in relative value and the dashed lines indicate the area of the cell. The horizontal axis indicates the time in units of 30 milliseconds, The indicated scale of 13 in the horizontal axis equals to 390 milliseconds. One pulse per second (pps) indicates that an electrical stimulation is applied at the rate of once a second. The photographs show the ATP distributions in the isolated cardiac muscle cells.

FIG. 19 shows changes of the area (dashed lines) and the ATP level of an isolated cardiac muscle cell when three different types of electrical stimulation (1 pulse per second (pps), 2 pps, and 3 pps) were applied. These results indicate that the changes in the ATP level and in the cell size were observed at the frequency of electrical pulses at 1 pps and 2 pps but were not observed at the frequency of electrical pulse at 3 pps. Accordingly, the cellular responsibility, including cell size and ATP level on the isolated cardiac muscle cells, to electrical stimulation varied depending on the frequency of the electrical pulse. These results suggest that monitoring ATP levels on isolated cardiac muscle cells is available for screening for a therapeutic agent that affects cardiac energy.

Figure 20:
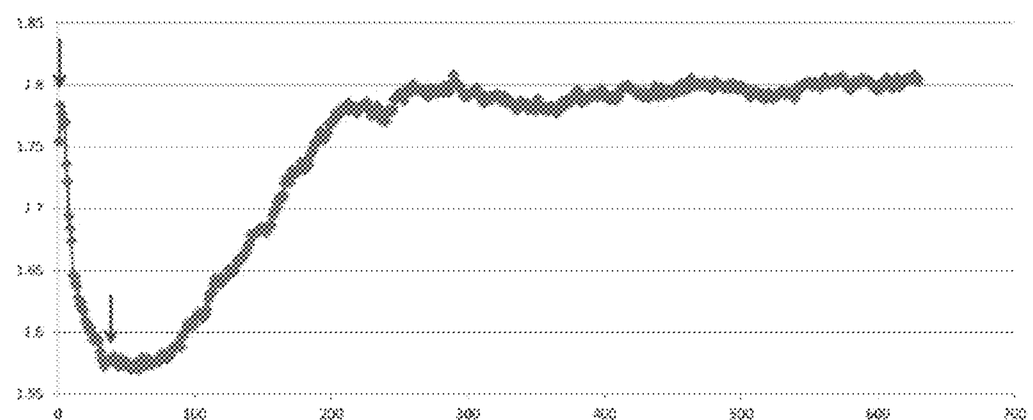
FIG. 20 is a line graph showing time-dependent changes in the ATP level in a tibialis anterior muscle which was obtained from a GO-ATeam 2-expressing transgenic mouse and to which electrical stimulations were applied for 30 seconds to induce muscle contractions. The arrow at time zero indicates the start of the electrical stimulations and the other arrow at 30 seconds indicates the end of the electrical stimulations. The vertical axis of the graph indicates the ATP level in relative value and the horizontal axis indicates the time in unit of second.

FIG. 20 shows dynamic changes in the ATP level on anterior tibial muscles in a transgenic mouse expressing GO-ATeam 2 when the electrical stimulation was applied to the ischiatic nerve of the mouse to induce muscle contraction. The transgenic mouse expressing GO-ATeam 2 was anesthetized and treated to expose the ischiatic nerve. Electric poles were attached to the exposed ischiatic nerve. The hair of the mouse was removed to expose anterior tibial muscles so that the ATP levels could be monitored with a fluorescence microscope system. The ischiatic nerve was electrically stimulated for 30 seconds. After the stimulation, ATP levels in the anterior tibial muscles recovered. The result suggests that monitoring ATP levels on muscles enables to assess the degree and rate of recovery after exercising and that the transgenic mouse which enables to visually investigate ATP levels is useful for the development of exercise apparatus and agents for strengthening muscles.

INDUSTRIAL APPLICABILITY

The transgenic mouse of the present invention is useful for research in the field of medical, pharmaceutical, sports sciences and also basic science.

The invention claimed is:

1. A transgenic mouse whose genome comprises a nucleic acid encoding a fusion protein, wherein the fusion protein comprises an ε subunit of an ATP synthase and two distinct fluorescent proteins as a donor and an acceptor for fluorescence resonance energy transfer (FRET); wherein the nucleic acid encoding the fusion protein which is inserted into the ROSA26 locus on the chromosome of the mouse; wherein one of the two distinct fluorescent proteins is placed at the amino terminal moiety of the ε subunit of the ATP synthase and the other is placed at the carboxyl terminal moiety of the ε subunit of the ATP synthase; wherein the ε subunit of the ATP synthase comprises the amino acid sequence set forth in SEQ ID NOs: 1, 2, or 3; and the DNA encoding the fusion protein is operably linked to a CAG promoter sequence, wherein said mouse expresses the fusion protein for measuring FRET signal that depends on an in vivo level of ATP.

2. The transgenic mouse according to claim 1, wherein the two distinct fluorescent proteins are a combination selected from the group consisting of a cyan fluorescent protein (CFP), a yellow fluorescent protein (YFP), a blue fluorescent protein (BFP), a green fluorescent protein (GFP), a red fluorescent protein (RFP) and an orange fluorescent protein (OFP).

3. The transgenic mouse according to claim 1, wherein the DNA encoding the fusion protein comprises a recombinase recognition sequences and a Stop sequence sandwiched between the recombinase recognition sequences; and the fusion protein is expressed following the removal of the Stop sequence sandwiched between the recombinase recognition sequences with a recombinase that recognizes the recognition sequences.

4. A method of evaluating the efficacy of a test substance to alter an ATP level, comprising the steps of:

(i) administering the test substance to the transgenic mouse expressing the fusion protein according to claim 1, (ii) measuring fluorescence emission arising from the fusion protein expressed in step (i), and (iii) evaluating the efficacy of the test substance to alter the ATP level by comparing the fluorescence emission measured in step (ii) as compared to fluorescence emission measured in said mouse prior to the administering the test substance.

5. The transgenic mouse according to claim 3, wherein the recombinase recognition sequences are selected from loxP, lox71, lox66, lox511, lox2272, Vlox (VCre), Slox (SCre) and FRT sequence.

6. The transgenic mouse according to claim 3, wherein the Stop sequence comprises a SV40pA sequence.

* * * * *

SEQUENCE LISTING

```
<160> NUMBER OF SEQ ID NOS: 3

<210> SEQ ID NO 1
<211> LENGTH: 133
<212> TYPE: PRT
<213> ORGANISM: Bacillus sp.

<400> SEQUENCE: 1
```

```
Met Lys Thr Ile His Val Ser Val Val Thr Pro Asp Gly Pro Val Tyr
1               5                   10                  15

Glu Asp Asp Val Glu Met Val Ser Val Lys Ala Lys Ser Gly Glu Leu
            20                  25                  30

Gly Ile Leu Pro Gly His Ile Pro Leu Val Ala Pro Leu Glu Ile Ser
        35                  40                  45

Ala Ala Arg Leu Lys Lys Gly Gly Lys Thr Gln Tyr Ile Ala Val Ser
    50                  55                  60

Gly Gly Phe Leu Glu Val Arg Pro Asp Lys Val Thr Ile Leu Ala Gln
65                  70                  75                  80

Ala Ala Glu Arg Ala Glu Asp Ile Asp Val Leu Arg Ala Lys Ala Ala
                85                  90                  95

Lys Glu Arg Ala Glu Arg Arg Leu Gln Ser Gln Gln Asp Asp Ile Asp
            100                 105                 110

Phe Lys Arg Ala Glu Leu Ala Leu Lys Arg Ala Met Asn Arg Leu Ser
        115                 120                 125

Val Ala Glu Met Lys
    130


<210> SEQ ID NO 2
<211> LENGTH: 132
<212> TYPE: PRT
<213> ORGANISM: Bacillus subtilis

<400> SEQUENCE: 2

Met Lys Thr Val Lys Val Asn Ile Val Thr Pro Asp Gly Pro Val Tyr
1               5                   10                  15

Asp Ala Asp Ile Glu Met Val Ser Val Arg Ala Glu Ser Gly Asp Leu
            20                  25                  30

Gly Ile Leu Pro Gly His Ile Pro Thr Val Ala Pro Leu Lys Ile Gly
        35                  40                  45

Ala Val Arg Leu Lys Lys Asp Gly Gln Thr Glu Met Val Ala Val Ser
    50                  55                  60

Gly Gly Phe Val Glu Val Arg Pro Asp His Val Thr Ile Leu Ala Gln
65                  70                  75                  80

Ala Ala Glu Thr Ala Glu Gly Ile Asp Lys Glu Arg Ala Glu Ala Ala
                85                  90                  95

Arg Gln Arg Ala Gln Glu Arg Leu Asn Ser Gln Ser Asp Asp Thr Asp
            100                 105                 110

Ile Arg Arg Ala Glu Leu Ala Leu Gln Arg Ala Leu Asn Arg Leu Asp
        115                 120                 125

Val Ala Gly Lys
    130


<210> SEQ ID NO 3
<211> LENGTH: 132
<212> TYPE: PRT
<213> ORGANISM: Bacillus subtilis

<400> SEQUENCE: 3

Met Lys Thr Val Lys Val Asn Ile Val Thr Pro Asp Gly Pro Val Tyr
1               5                   10                  15

Asp Ala Asp Ile Glu Met Val Ser Val Arg Ala Glu Ser Gly Asp Leu
            20                  25                  30

Gly Ile Leu Pro Gly His Ile Pro Thr Val Ala Pro Leu Lys Ile Gly
        35                  40                  45
```

-continued

```
Ala Val Arg Leu Lys Lys Asp Gly Gln Thr Glu Met Val Ala Val Ser
    50                  55                  60

Gly Gly Phe Val Glu Val Arg Pro Asp His Val Thr Ile Leu Ala Gln
65                  70                  75                  80

Ala Ala Glu Thr Ala Glu Gly Ile Asp Lys Glu Arg Ala Glu Ala Ala
                85                  90                  95

Arg Gln Arg Ala Gln Glu Arg Leu Asn Ser Gln Ser Asp Asp Thr Asp
            100                 105                 110

Ile Arg Arg Ala Glu Leu Ala Leu Gln Lys Ala Leu Asn Lys Leu Asp
        115                 120                 125

Val Ala Gly Lys
    130
```